(12) United States Patent
Li et al.

(10) Patent No.: US 10,321,715 B2
(45) Date of Patent: Jun. 18, 2019

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Xianming Wang, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 191 days.

(21) Appl. No.: 15/218,062

(22) Filed: Jul. 24, 2016

(65) Prior Publication Data

US 2016/0324219 A1    Nov. 10, 2016

(30) Foreign Application Priority Data

Aug. 4, 2015    (CN) .................... 2015 2 0577779 U

(51) Int. Cl.
| | |
|---|---|
| *A24F 47/00* | (2006.01) |
| *A61M 15/06* | (2006.01) |
| *A61M 11/04* | (2006.01) |
| *F16J 15/02* | (2006.01) |

(52) U.S. Cl.
CPC ......... *A24F 47/008* (2013.01); *A61M 11/042* (2014.02); *A61M 15/06* (2013.01); *F16J 15/021* (2013.01)

(58) Field of Classification Search
None
See application file for complete search history.

(56) References Cited

U.S. PATENT DOCUMENTS

| | | | | |
|---|---|---|---|---|
| 3,938,947 A | * | 2/1976 | Rosenthal | F17C 13/04 251/121 |
| 4,431,119 A | * | 2/1984 | Stoody | B65D 83/62 222/129 |
| 4,770,445 A | * | 9/1988 | Steer | A61F 5/4405 285/110 |
| 4,921,618 A | * | 5/1990 | Hamlin | B01D 17/0214 210/780 |
| 5,547,131 A | * | 8/1996 | Brace | A61M 15/0065 128/200.23 |
| 5,908,256 A | * | 6/1999 | Bernstein | A45D 34/04 401/136 |
| 6,558,180 B2 | * | 5/2003 | Nishimoto | H01R 9/223 439/271 |

(Continued)

*Primary Examiner* — Thor S Campbell
(74) *Attorney, Agent, or Firm* — Cheng-Ju Chiang

(57) ABSTRACT

The present disclosure relates to an exemplary atomizer for coupling with a power supply to form an electronic cigarette. The atomizer includes a liquid supply and a connecting component. The liquid supply is configured for storing tobacco liquid. The connecting component is configured for connecting the liquid supply and the power supply. The connecting component includes a liquid conducting element and a heating element in contact with the liquid conducting element. The connecting component has a first end and an opposite second end. The first end is configured for connecting the liquid supply, and the second end is configured for connecting the power supply. The liquid supply is detachably engaged with the connecting component by snap fit.

8 Claims, 6 Drawing Sheets

(56) References Cited

U.S. PATENT DOCUMENTS

| | | | | |
|---|---|---|---|---|
| 8,631,863 B2* | 1/2014 | Heckel | | E21B 33/1208 |
| | | | | 166/229 |
| 8,794,313 B2* | 8/2014 | Heckel | | E21B 41/00 |
| | | | | 166/229 |
| 8,997,753 B2* | 4/2015 | Li | | H01C 17/00 |
| | | | | 128/202.21 |
| 9,254,007 B2* | 2/2016 | Liu | | A24F 47/008 |
| 9,622,511 B2* | 4/2017 | Zhu | | A24F 47/008 |
| 9,839,237 B2* | 12/2017 | Chang | | A24F 47/008 |
| 2012/0111347 A1* | 5/2012 | Hon | | A24F 47/008 |
| | | | | 131/329 |
| 2013/0180533 A1* | 7/2013 | Kim | | A24F 47/008 |
| | | | | 131/273 |
| 2013/0228191 A1* | 9/2013 | Newton | | A24F 47/008 |
| | | | | 131/329 |
| 2014/0060524 A1* | 3/2014 | Liu | | A24F 47/008 |
| | | | | 128/200.14 |
| 2014/0299139 A1* | 10/2014 | Liu | | A24F 47/008 |
| | | | | 131/329 |
| 2014/0360514 A1* | 12/2014 | Zhu | | A24F 47/008 |
| | | | | 131/329 |
| 2015/0114410 A1* | 4/2015 | Doster | | A24F 47/008 |
| | | | | 131/329 |
| 2015/0144145 A1* | 5/2015 | Chang | | A24F 47/008 |
| | | | | 131/328 |
| 2015/0181939 A1* | 7/2015 | Liu | | A24F 47/008 |
| | | | | 131/329 |
| 2015/0313275 A1* | 11/2015 | Anderson | | A24B 15/10 |
| | | | | 131/352 |
| 2015/0313288 A1* | 11/2015 | Liu | | A24F 47/008 |
| | | | | 131/329 |
| 2016/0007654 A1* | 1/2016 | Zhu | | A24F 47/008 |
| | | | | 131/328 |
| 2016/0044963 A1* | 2/2016 | Saleem | | A24F 47/008 |
| | | | | 131/328 |
| 2016/0120223 A1* | 5/2016 | Keen | | A24F 47/00 |
| | | | | 131/329 |
| 2016/0278436 A1* | 9/2016 | Verleur | | A24F 47/008 |
| 2016/0332754 A1* | 11/2016 | Brown | | B65B 3/10 |
| 2017/0006917 A1* | 1/2017 | Alvarez | | A24F 47/008 |
| 2017/0135401 A1* | 5/2017 | Dickens | | A24F 47/008 |

* cited by examiner

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

An atomizer for an electronic cigarette mainly includes two types: a disposable atomizer and a refillable atomizer. The disposable atomizer is usually filled with tobacco liquid before leaving factory. However, high risk of liquid leakage may exist during transportation.

What are needed, therefore, are an atomizer and an electronic cigarette using same, which can overcome the above shortcomings.

SUMMARY

The present disclosure relates to an exemplary atomizer for coupling with a power supply to form an electronic cigarette. The atomizer includes a liquid supply and a connecting component. The liquid supply is configured for storing tobacco liquid. The connecting component is configured for connecting the liquid supply and the power supply. The connecting component includes a liquid conducting element and a heating element in contact with the liquid conducting element. The connecting component has a first end and an opposite second end. The first end is configured for connecting the liquid supply, and the second end is configured for connecting the power supply. The liquid supply is detachably engaged with the connecting component by snap fit.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
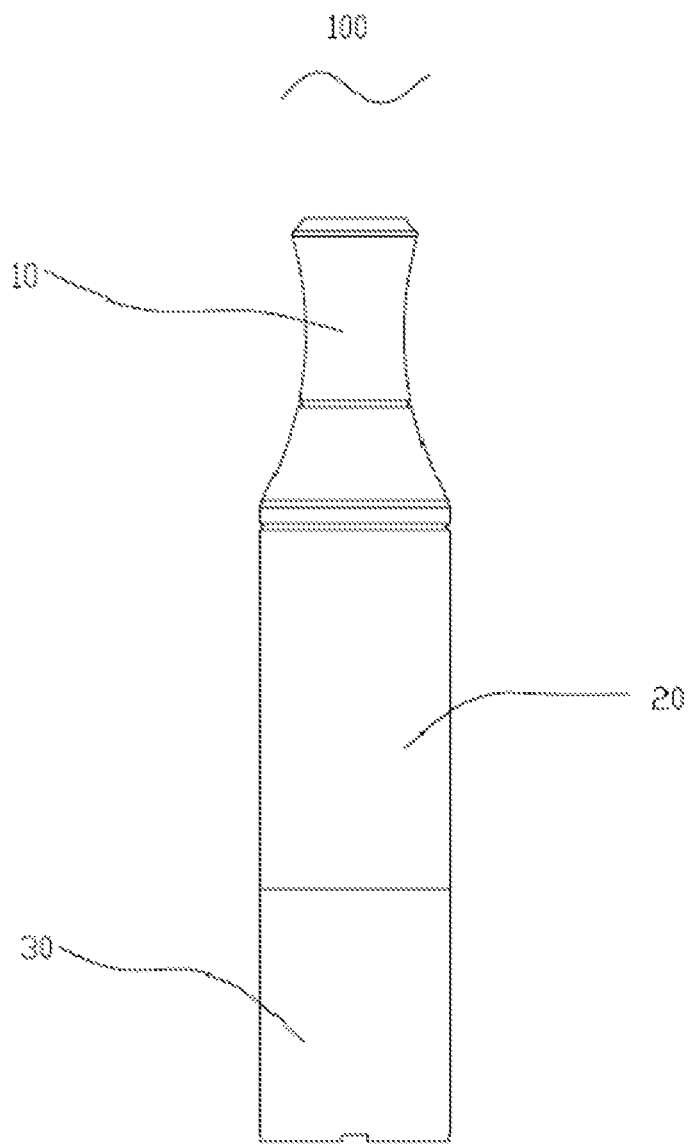
FIG. 1 is a side view of an atomizer according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
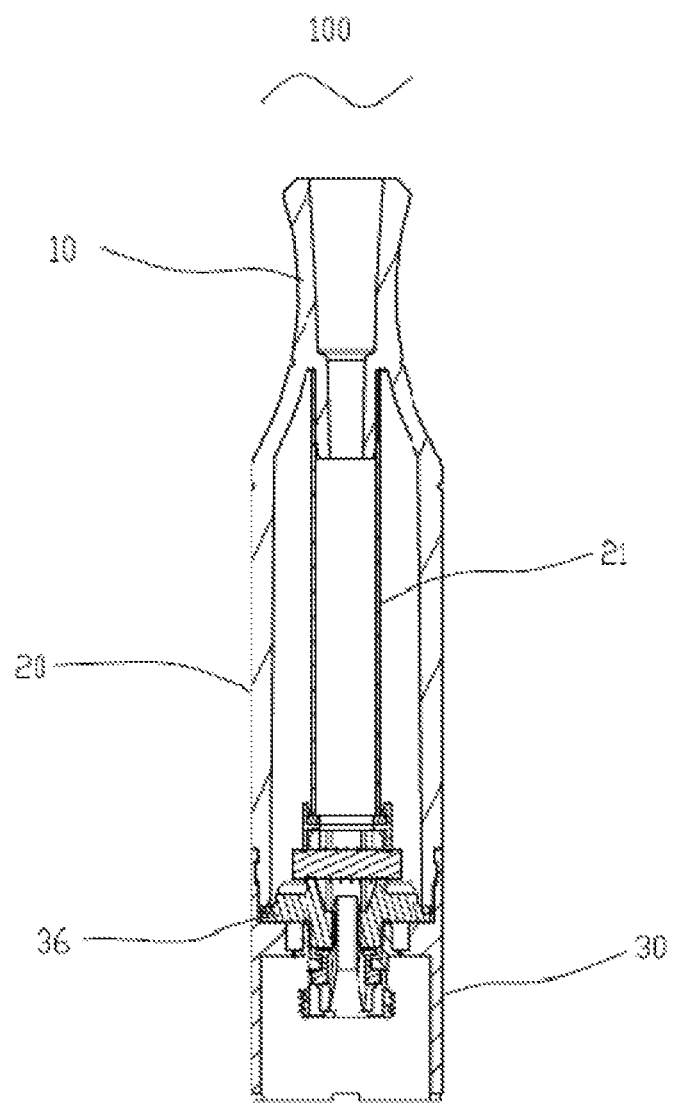
FIG. 2 is a side cross-sectional view of the atomizer of FIG. 1.
Figure 3:
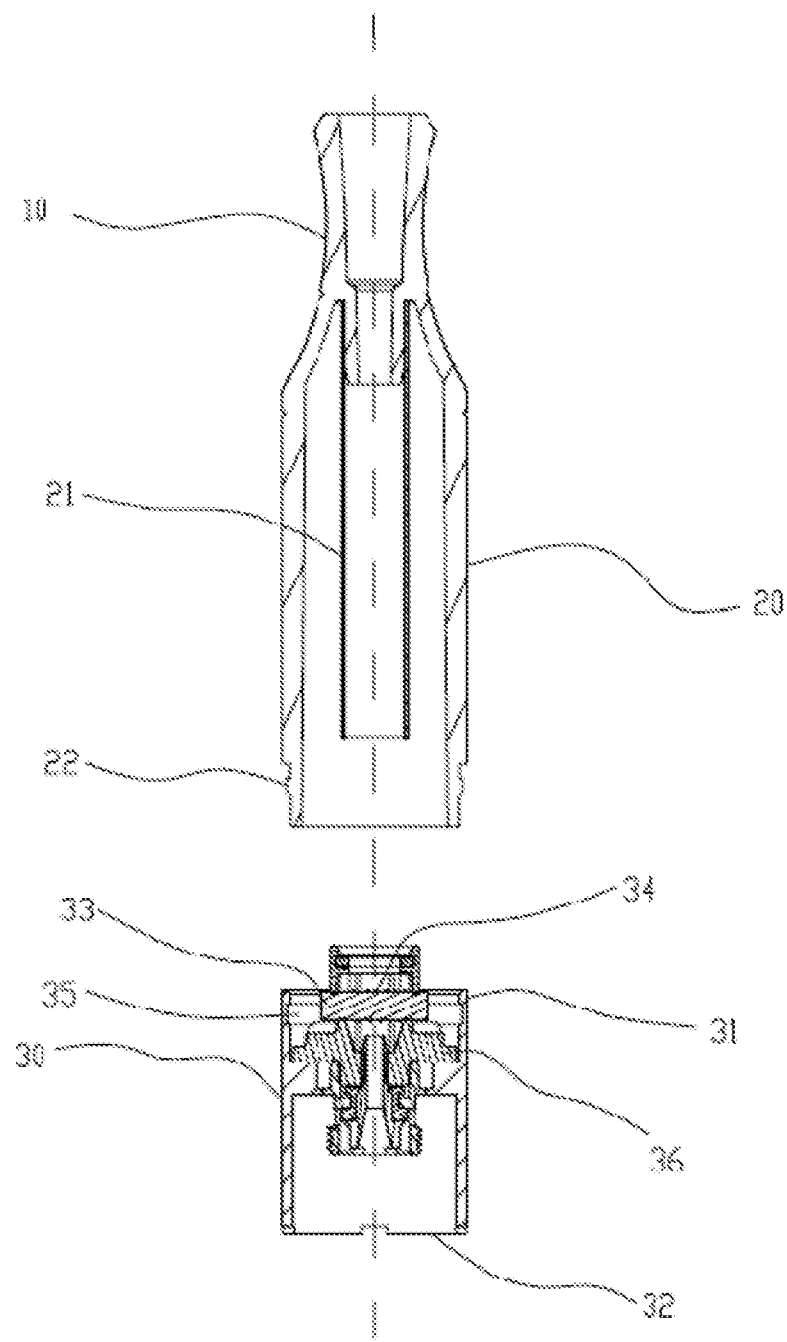
FIG. 3 is a side cross-sectional view of a liquid supply and a connecting component being separated from each other.
Figure 6:
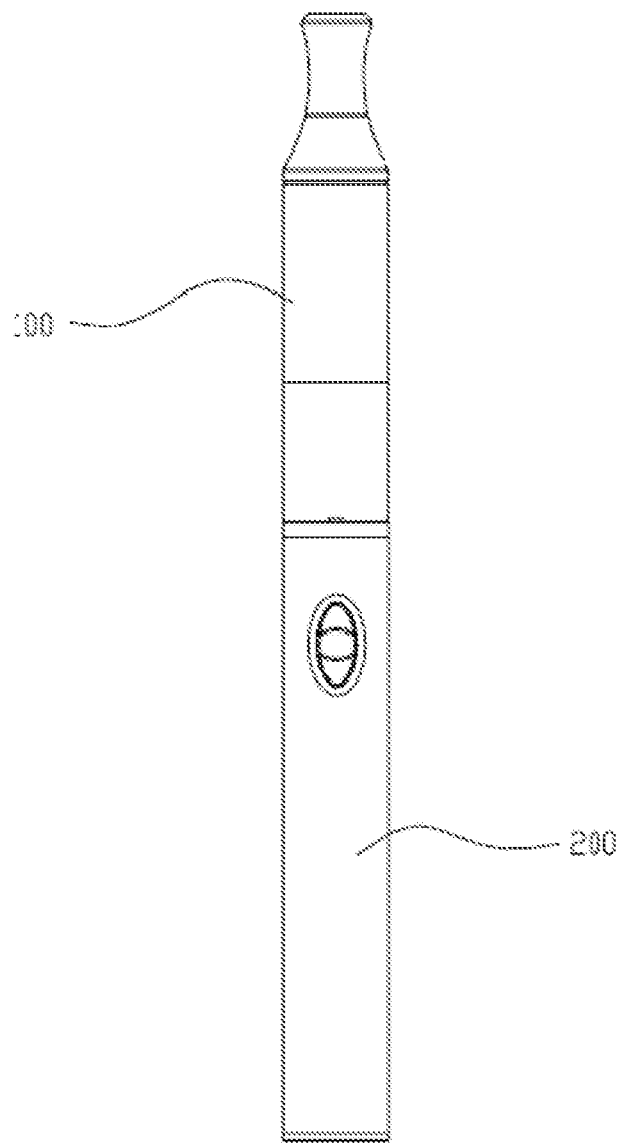
FIG. 6 is a side view of an electronic cigarette according to a second embodiment.

Referring to FIG. 1, an atomizer 100 is shown. The atomizer 100 is configured (i.e., structured and arranged) for coupling with a power supply 200 to form an electronic cigarette (as seen in FIG. 6). Referring to FIGS. 2-3, the atomizer 100 includes a liquid supply 20 for storing tobacco liquid, and a connecting component 30 configured for connecting the liquid supply 20 and the power supply 200. The connecting component 30 includes a liquid conducting element 33 and a heating element 34 in contact with the liquid conducting element 33. The connecting component 30 has a first end 31 and a second end 32. The first end 31 is configured for connecting with the liquid supply 20, while the second end 32 is configured for connecting with the power supply 200. The liquid supply 20 is detachably connected to the connecting component 30 by snap fit. In the present embodiment, the liquid conducting element 33 is made of ceramic material or glass fiber, a resistance of the heating element 34 is in an approximate range from $1.5\Omega$ to $2.0\Omega$.

Figure 4:
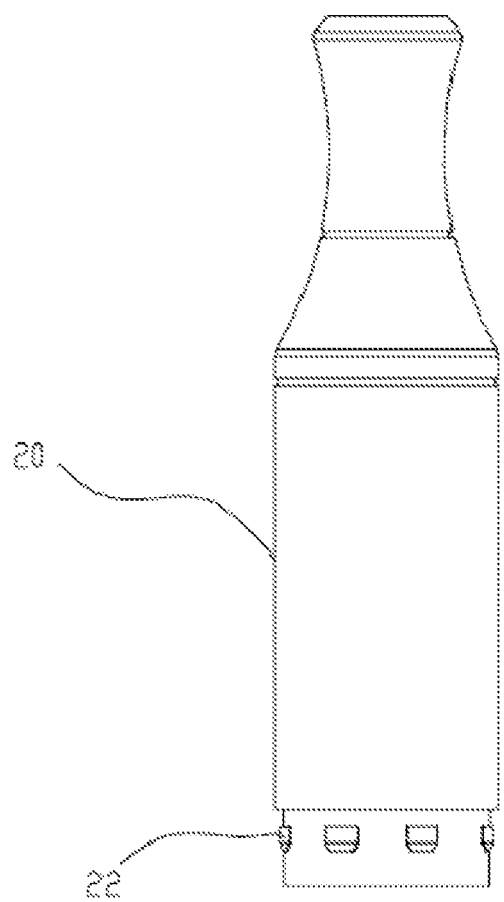
FIG. 4 is a side view of a liquid supply with a latching part of an embodiment.
Figure 5:
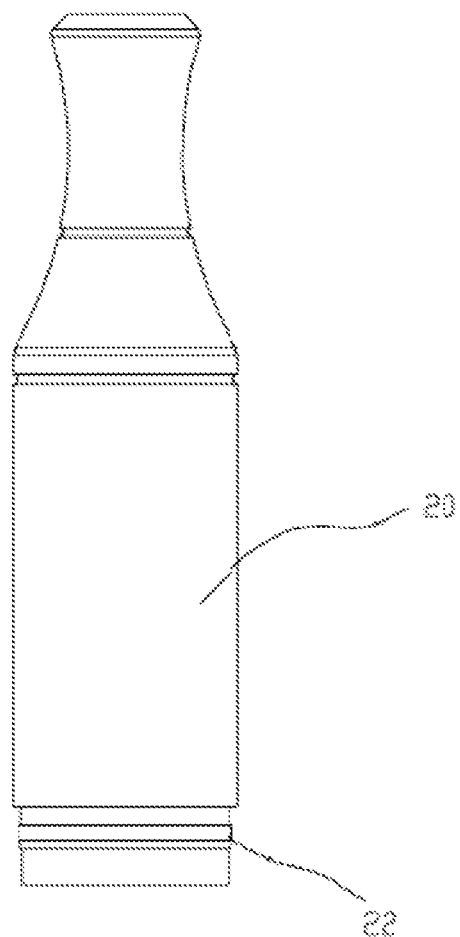
FIG. 5 is a side view of a liquid supply with a latching part as a variation of FIG. 4.

Referring to FIGS. 3-4, the liquid supply 20 includes a protruding latching part 22 on an exterior surface, and the connecting component 30 defines a groove 35 configured for coupling with the latching part 22. In the present embodiment, the latching part 22 includes at least two arc-shaped protrusions. In other embodiments, the latching part 22 may be an annular protrusion as seen in FIG. 5.

Referring to FIG. 2, the atomizer 100 further includes a mouthpiece 10 integrally formed with the liquid supply 20. The liquid supply 20 includes an air pipe 21 connecting the connecting component 30 and the mouthpiece 10.

The connecting component 30 further includes a sealing ring 36. After the liquid supply 20 is coupled with the connecting component 30, the liquid supply 20 abuts against the sealing ring 36 to seal the liquid supply 20.

In the present embodiment, the atomizer 100 includes two independent components, i.e., the liquid supply 20 and the connecting component 30. The liquid supply 20 and the connecting component 30 are coupled by snap fit. In use, after tobacco liquid is filled in the liquid supply 20, the liquid supply 20 is assembled with the connecting component 30 easily, and then the atomizer 100 can be used. Accordingly, it is unnecessary to fill the liquid supply 20 with tobacco liquid during transportation, thus eliminating risk of liquid leakage. During transportation, a dust proof cover may be provided at a connection end of the connecting component 30.

It is to be understood that in other embodiments, the connecting component 30 may include a protruding latching part inside, and the liquid supply 20 may include a groove matching with the latching part on an exterior surface.

Referring to FIG. 6, an electronic cigarette includes the above atomizer 100 and the power supply 200. The atomizer 100 and the power supply 200 are detachably coupled with each other via screw threads.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer for coupling with a power supply to form an electronic cigarette, comprising:
    a liquid supply configured for storing tobacco liquid; and
    a connecting component disposed and located between the liquid supply and the power supply, and configured for connecting the liquid supply and the power supply, the connecting component comprising a liquid conducting element and a heating element in contact with the liquid conducting element, the connecting component having a first end and an opposite second end, the first end being configured for connecting the liquid supply, the second end being configured for connecting the power supply, the liquid supply and the connecting component being detachably engaged with each other by snap fit, wherein the liquid conducting element is disposed at the first end of the connecting component to be exposed to the liquid supply for absorbing the tobacco liquid of the liquid supply;
    wherein the connecting component comprises a sealing ring inside to abut against a side of the liquid conducting element, and the liquid supply abuts against the sealing ring when the liquid supply is engaged with the connecting component.

2. The atomizer according to claim 1, wherein the liquid supply comprises a protruding latching part on an exterior surface, and the connecting component defines a groove matching with the latching part.

3. The atomizer according to claim 1, wherein the connecting component comprises a protruding latching part inside, the liquid supply defines a groove on an exterior surface, and the groove is configured for coupling with the latching part.

4. The atomizer according to claim 2, wherein the latching part comprises an annular protrusion.

5. The atomizer according to claim 2, wherein the latching part comprises at least two arc-shaped protrusions.

6. The atomizer according to claim 1, further comprising a mouthpiece integrally formed with the liquid supply, wherein the liquid supply comprises an air pipe connecting the connecting component and the mouthpiece by abutting against the first end of the connecting component via a distal end of the air pipe.

7. The atomizer according to claim 1, wherein the liquid conducting element is made of ceramic material or glass fiber, and a resistance of the heating element is in a proximate range from $1.5\Omega$ to $2\Omega$.

8. An electronic cigarette, comprising:
    an atomizer according to claim 1; and a power supply, the power supply being configured for supplying the atomizer power.

* * * * *